United States Patent [19]

Hay

[11] 4,033,982
[45] July 5, 1977

[54] 3,4,5-TRITHIAPOLYCYCLO COMPOUNDS AND DERIVATIVES

[75] Inventor: Allan Stuart Hay, Schenectady, N.Y.

[73] Assignee: General Electric Company, Schenectady, N.Y.

[22] Filed: Jan. 21, 1976

[21] Appl. No.: 651,190

Related U.S. Application Data

[63] Continuation-in-part of Ser. No. 515,349, Oct. 16, 1974, abandoned.

[52] U.S. Cl. .......................................... 260/327 H
[51] Int. Cl.² ...................................... C07D 341/00
[58] Field of Search ............................. 260/327 H

[56] References Cited

UNITED STATES PATENTS 3,586,700  6/1971  Kurtz et al. .................. 260/327

*Primary Examiner*—Cecilia M. S. Jaisle
*Attorney, Agent, or Firm*—F. Wesley Turner; Joseph T. Cohen; Jerome C. Squillaro

[57] ABSTRACT

A process for the preparation of 3,4,5-trithiapolycyclo compounds is described which comprises the reaction of sulfur with bicyclo[2.2.1]hept-2-ene compounds carried out in the presence of (1) a phenol, and (2) a base. The process can be carried out either in the absence or presence of an inert organic solvent. The trithiapolycyclic compounds produced by this process are useful as monomers in the synthesis of polymers which can be employed as additives for lubricants, to produce effective coatings on solid substrates, or to produce fibers and films.

7 Claims, No Drawings

3,4,5-TRITHIAPOLYCYCLO COMPOUNDS AND DERIVATIVES

This is a continuation-in-part of application Ser. No. 515,349, filed Oct. 16, 1974 and now abandoned.

This invention relates to a process for the preparation of a 3,4,5-trithiapolycyclo compounds under reaction conditions which comprise the reaction of sulfur with bicyclo[2.2.1]hept-2-ene compounds carried out in the presence of (1) a phenol, and (2) a base. The process can be carried out either in the absence or in the presence of an inert organic solvent.

Various observations have been made by the prior art regarding reactions between sulfur and organic compounds carried out in the presence of a base, both in the absence as well as in the presence of various solvents, such as those described in my description of the preparation of (a) organomercaptophenols, and (b) thiobis-2,6-disubstituted phenols from the reactions of sulfur and a phenol, set out in my copending patent applications Ser. Nos. 484,986, now U.S. Pat. No. 3,952,063, of Ser. No. 484,995, now U.S. Pat. No. 3,953,519, and 484,996, now U.S. Pat. No. 3,979,460, filed July 1, 1974, assigned to the same assignee as the assignee of this invention, and A. N. Kurtz et al.'s description of the preparation of 3,4,5-trithiapolycyclo compounds by the reaction of bicyclo[2.2.1]hept-2-ene compounds and sulfur carried out in the presence of ammonia and dipolar aprotic solvents, set out in U.S. Pat. No. 3,586,700, issued June 22, 1971, among others.

Essentially, my invention comprises a process for the preparation of 3,4,5-trithiapolycyclo compounds which comprises contacting a bicyclo[2.2.1]hept-2-ene compound and sulfur in the presence of (1) a phenol, and (2) a base. The process can be carried out either in the absence or presence of an inert organic solvent.

In my process, any bicyclo[2.2.1]hept-2-ene compound (also known as norbornenes) or mixtures thereof, can be reacted with sulfur. Representative of bicyclo[2.2.1]hept-2-ene compounds suited to this invention are those described by the general formula:

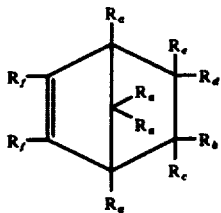

Formula (A)

wherein each of $R_a$, $R_b$, $R_c$, $R_d$ and $R_e$ when taken singly can be hydrogen; halogen; alkyl of from 1 to about 15 carbon atoms such as methyl, ethyl, propyl, pentyl, octyl, 2-ethylhexyl, nonyl, decyl, dodecyl, pentadecyl, and the like; aryl of from 6 to about 15 carbon atoms such as phenyl, naphthyl, benzyl, phenethyl, alpha mesityl, naphthyl, tolyl, xylyl, mesityl, methylnaphthyl and the like; and cycloalkyl of from 4 to about 10 carbon atoms such as cyclobutyl, cyclopentyl, methylcyclopentyl, dimethylcyclopentyl, ethylcyclopentyl, cyclohexyl, methylcyclohexyl, cyclopentyl, and the like; $R_b$ and $R_d$ when taken singly can also be alkenyl of from 2 to about 10 carbon atoms such as vinyl, propenyl, allyl, 1-butenyl, 2-butenyl, 3-butenyl, pentenyl, hexenyl, 2-ethylhexenyl, decenyl, and the like; hydroxyl; hydroxyalkyl containing from 1 to about 10 carbon atoms such as hydroxymethyl, hydroxyethyl, hydroxypropyl, 2-hydroxypropyl, hydroxypentyl, hydroxyoctyl, hydroxydecyl, and the like; dialkylamino wherein the alkyl group contains from 1 to about 10 carbon atoms such as N,N-dimethylamino, N,N-diethylamino, N,N-dipropylamino, N,N-dibutylamino, N,N-didecylamino and the like; dialkylaminoalkyl wherein the alkyl group contains from 1 to about 4 carbon atoms such as N,N-dimethylaminoethyl, N,N-dipropylaminobutyl, and the like; and alkoxy having from 1 to about 10 carbon atoms such as methoxy, ethoxy, pentoxy, cyclopentoxy, hexoxy, cyclohexoxy, decoxy, and the like; $R_f$ can be hydrogen or alkyl of from 1 to about 15 carbon atoms, as previously shown; $R_b$ and $R_c$ taken together and $R_d$ and $R_e$ taken together are alkylidene of from 1 to about 6 carbon atoms such as methylene, ethylidene, propylidene, butylidene, pentylidene, hexylidene, and the like; $R_b$ and $R_d$ taken together are the divalent $$-CHYCH=CY-$$

group in which Y is hydrogen or methyl. It is understood that the substituents on the bicycloheptyl ring can be either linear or branched; these variations are known to those skilled in the art. The preferred bicyclo[2.2.1]hept-2-ene compounds are usually those that have not more than two substituents on the bicyclic moiety and those in which the hydrogen atom on the bridge carbon atom is syn.

Illustrative of suitable norbornene compounds one can mention:
5-hydroxybicyclo[2.2.1]hept-2-ene,
5-methylbicyclo[2.2.1]hept-2-ene,
5-hydroxymethylbicyclo[2.2.1]hept-2-ene,
5-hydroxybutylbicyclo[2.2.1]hept-2-ene,
5-N,N-dimethylaminoethylbicyclo[2.2.1]hept-2-ene,
5-N,N-dipropylaminobutylbicyclo[2.2.1]hept-2-ene,
5,6-dihydroxybicyclo[2.2.1]hept-2-ene,
5-N,N-dimethylamino-6-N,N-dimethylaminobicyclo[2.2.1]hept-2-ene,
5,6-di-(N,N-dimethylaminobicyclo[2.2.1]hept-2-ene,
5,6-diethylbicyclo[2.2.1]hept-2-ene,
5,6-di-(hydroxypropyl)-bicyclo[2.2.1]hept-2-ene,
bicyclo[2.2.1]hept-5-en-2-yl ethyl ether,
bicyclo[2.2.1]hept-5-en-2-yl ethyl sulfide,
1-(bicyclo[2.2.1]hept-5-en-2-yl)-1,3-propanediol,
bicyclo[2.2.1]hept-5-en-2-ylmethyl cyclopentyl ether,
bicyclo[2.2.1]hept-5-en-2-ylmethyl cyclohexyl ether,
4-oxatricyclo[5.2.1.0$^{2,6}$]dec-8-ene,
4-thiatricyclo[5.2.1.0$^{2,6}$]dec-8-ene,
bicyclo[2.2.1]hept-2-ene,
1-methylbicyclo[2.2.1]hept-2-ene,
5-methylbicyclo[2.2.1]hept-2-ene,
5-methyl-6-chlorobicyclo[2.2.1]hept-2-ene,
1-ethylbicyclo[2.2.1]-hept-2-ene,
5-ethylbicyclo[2.2.1]hept-2-ene,
5-isopropylbicyclo[2.2.1]hept-2-ene,
5-pentylbicyclo[2.2.1]hept-2-ene,
5-heptylbicyclo[2.2.1]hept-2-ene,
5-heptyl-6-hydroxybicyclo[2.2.1]hept-2-ene,
5-(2-ethylhexyl)bicyclo[2.2.1]hept-2-ene,
1-nonylbicyclo[2.2.1]hept-2-ene,
5-nonylbicyclo[2.2.1]hept-2-ene,
5-dodecylbicyclo[2.2.1]hept-2-ene,
5-pentadecylbicyclo[2.2.1]hept-2-ene, 5,5-dimethylbicyclo[2.2.1]hept-2-ene,
5,5-diisopropylbicyclo[2.2.1]hept-2-ene,
5,5-dibutylbicyclo[2.2.1]hept-2-ene,
5,5-dihexylbicyclo[2.2.1]hept-2-ene,
5-methyl-5-ethylbicyclo[2.2.1]hept-2-ene,
5,5-didecylbicyclo[2.2.1]hept-2-ene,
5,6-dimethylbicyclo[2.2.1]hept-2-ene,
5-methyl-6-ethylbicyclo[2.2.1]hept-2-ene,
5,6-dipropylbicyclo[2.2.1]hept-2-ene,
5,6-diisopropylbicyclo[2.2.1]hept-2-ene,
5,6-dipentylbicyclo[2.2.1]hept-2-ene,
5,6-di(2-ethylhexyl)bicyclo[2.2.1]hept-2-ene,
5,6-didodecylbicyclo[2.2.1]hept-2-ene,
5,5,6-trimethylbicyclo[2.2.1]hept-2-ene,
5,5,6-tripropylbicyclo[2.2.1]hept-2-ene,
5,5-dimethyl-6-ethylbicyclo[2.2.1]hept-2-ene,
5,5,6,6-tetramethylbicyclo[2.2.1]hept-2-ene,
5,5,6,6-tetraisopropylbicyclo[2.2.1]hept-2-ene,
5,5-dimethyl-6,6-diethylbicyclo[2.2.1]hept-2-ene,
1-phenylbicyclo[2.2.1]hept-2-ene,
5-phenylbicyclo[2.2.1]hept-2-ene,
5-naphthylbicyclo[2.2.1]hept-2-ene,
5,5-diphenylbicyclo[2.2.1]hept-2-ene,
5,6-diphenylbicyclo[2.2.1]hept-2-ene,
5-benzylbicyclo[2.2.1]hept-2-ene,
5-phenethylbicyclo[2.2.1]hept-2-ene,
5,6-dibenzylbicyclo[2.2.1]hept-2-ene,
5-α-mesitylbicyclo[2.2.1]hept-2-ene,
5-tolylbicyclo[2.2.1]hept-2-ene,
5,6-ditolylbicyclo[2.2.1]hept-2-ene,
5-xylylbicyclo[2.2.1]hept-2-ene,
5-methylnaphthylbicyclo[2.2.1]hept-2-ene,
5-cyclobutylbicyclo[2.2.1]hept-2-ene,
5,6-dicyclopentylbicyclo[2.2.1]hept-2-ene,
5-methylcyclopentylbicyclo[2.2.1]hept-2-ene,
5-isopropylcyclopentylbicyclo[2.2.1]hept-2-ene,
5-cyclohexylbicyclo[2.2.1]hept-2-ene,
5-methylenebicyclo[2.2.1]hept-2-ene,
5-ethylidenebicyclo[2.2.1]hept-2-ene,
5-propylidenebicyclo[2.2.1]hept-2-ene,
5-butylidenebicyclo[2.2.1]hept-2-ene,
5-hexylidenebicyclo[2.2.1]hept-2-ene,
5,6-dimethylenebicyclo[2.2.1]hept-2-ene,
5,6-diethylidenebicyclo[2.2.1]hept-2-ene,
5-methyl-6-ethylidenebicyclo[2.2.1]hept-2-ene,
5-hydroxymethyl-6-methylenebicyclo[2.2.1]hept-2-ene,
5-vinylbicyclo[2.2.1]hept-2-ene,
5-allylbicyclo[2.2.1]hept-2-ene,
5-(3-butenyl)bicyclo[2.2.1]hept-2-ene,
5-(4-pentenyl)bicyclo[2.2.1]hept-2-ene,
5-(2-methylbut-3-enyl)bicyclo[2.2.1]hept-2-ene,
5-(5-hexenyl)bicyclo[2.2.1]hept-2-ene,
5-propenylbicyclo[2.2.1]hept-2-ene,
5-isopropenylbicyclo[2.2.1]hept-2-ene,
5-allyl-5-methylbicyclo[2.2.1]hept-2-ene,
5-propenyl-6-methylbicyclo[2.2.1]hept-2-ene,
5-methylene-6-methylbicyclo[2.2.1]hept-2-ene,
5-methylene-6-propylbicyclo[2.2.1]hept-2-ene,
5-vinyl-6-ethylbicyclo[2.2.1]hept-2-ene,
5-(5-hexenyl)-6-methylbicyclo[2.2.1]hept-2-ene,
and the like.

Sulfur can be employed in any of its elemental forms or as polysulfide ions represented by the generic formula $M_yS_x$ wherein $x$ is a positive integer at least equal to 2 and wherein M is selected from the group consisting of alkali and alkaline earth metals as well as ammonium ions $R_4N^+$ where R is hydrogen or a hydrocarbon.

Preferably, elemental sulfur is employed. Because of its economic advantage, elemental sulfur can be employed in any of the commonly known commercial forms, such as bright sulfur (99.5%), dark sulfur (up to 1% carbonaceous material); refined sulfur (99.8%); high purity sulfur (99.97%); sublimed sulfur (flowers of sulfur); flour sulfur, ground refined or crude sulfur in various mesh sizes; and Rubbermakers, a ground special grade.

Any base that can be employed which will dissolve in the reaction mixture which is capable of forming in the presence of a phenol a metal phenoxide (sometimes referred to as a metal phenolate). The presence of a phenoxide ion in the reaction mixture is believed to be an essential reaction intermediate in the process of this invention.

Representative of base, i.e. basic species, which can be employed are elemental alkali and alkaline earth metals, alkali or alkaline earth metal hydroxides, and salts of strong bases and weak organic acids; etc. Specific examples include sodium, potassium, and magnesium metal; sodium, potassium, lithium, and calcium hydroxide; sodium, lithium, and barium carbonates, sodium acetate, sodium benzoate, sodium methylate, sodium thiosulfate, sodium sulfide, sodium tetrasulfide, sodium cyanate, etc. Preferred basic species are the metals sodium and potassium, sodium and potassium hydroxides and salts of sodium and potassium bases and weak organic acids.

Any phenol can be employed which has at least one —OH radical directly bonded to an aromatic ring carbon atom. Phenols suited to the practice of the invention can be described by the following formula:

Formula (B)

wherein Ar is at least a monovalent arene radical having at least one —OH radical attached directly to an arene carbon atom, R is an alkyl, cycloalkyl, aryl, halide, hydroxy, alkoxy, alkanoate radical or a combination thereof, $m$ is a positive integer at least equal to 0, and $n$ is a positive integer at least equal to 1. Presently preferred phenols contain from 6 to 30, more preferably from 6 to 15, and even more preferably from 6 to 8 carbon atoms.

Broadly, however, subject to the proviso that at least one hydroxyl radical is attached directly to an arene ring carbon atom, the arene radical of Formula (B) can be any monocyclic or polycyclic organic radical having any other substituents other than hydrogen, attached directly to any acyclic or cyclic carbon atom subject to the proviso that the substituents do not interfere with the formation of a phenoxide ion. Accordingly, the arene substituents can be (1)(a) any acyclic or cyclic organic radical, e.g. alkyl, cycloalkyl, aryl, aralkyl, alkaryl, alkcycloalkyl, cycloalkaryl radicals, etc., or combinations thereof, etc., including acyclic and cyclic radicals having any noninterfering constituents such as halide, i.e. —Cl, —Br, —I; hydroxy, i.e. —OH; alkoxy, i.e. —$OR^1$; and alkanoate, i.e. —$OOCR^1$ radicals, $R^1$ in all cases being an alkyl group; or can be (1)(b) any noninterfering constituent set out in (1)(a) hereinbefore. Illustrative of presently preferred phenols of Formula (B) which can be employed are the following:
phenol
o-cresol m-cresol
p-cresol
2,3-xylenol
3,4-xylenol
2,5-xylenol
2,6-xylenol
3,4-xylenol
3,5-xylenol
o-ethylphenol
m-ethylphenol
p-ethylphenol
2,3,4-trimethylphenol
2.4.5-trimethylphenol
2,4,6-trimethylphenol
o-isopropylphenol
m-isopropylphenol
p-isopropylphenol
o-sec-butylphenol
p-sec-butylphenol
o-tert-butylphenol
m-tert-butylphenol
p-tert-butylphenol
p-tert-amylphenol
p-(cyclopenten-2-yl)phenol
p-cyclohexylphenol
o-phenylphenol
p-phenylphenol
p-(1,1,3,3-tetramethylbutyl)phenol
2,4-di-tert-butylphenol
2,6-di-tert-butylphenol
p-nonylphenol
2,4,6-tri-tert-butylphenol
p-dodecylphenol
α-naphthol
β-naphthol
4-hydroxyindan
5-hydroxyindan
2,2'-methylenediphenol
2,4'-methylenediphenol
4,4'-methylenediphenol
4,4'-isopropylidenediphenol
4,4'-(2-butylidene)diphenol
4,4'-[2-(3-methyl)butylidene]diphenol
4,4'-(cyclohexylidene)diphenol
4,4'-(3,3',5,5'-tetra-tert-butyl)isopropylidenediphenol
4,4'-dihydroxydiphenyl sulfone, etc.

Especially presently preferred phenols in the practice of this invention are 2,6-dialkylphenols wherein each alkyl group contain from 1 to 4 carbon atoms, more especially preferred is 2,6-dimethylphenol (also known as 2,6-xylenol) because of its current extended commercial availability.

In general, the process can be carried out in the absence of any solvent employing a phenol as the sole solvent species in the process of this invention. In addition to a phenol, the process can be carried out in the presence of any inert organic solvent, preferably selected from nonpolar organic solvents such as aliphatic and aromatic hydrocarbons such as hexane, 3-methylpentane, heptane, cyclohexane, methylcyclohexane, cyclohexane, isooctane, p-cymene, cumene, toluene, benzene, etc., or low-polar, low-dielectric constant solvents, i.e. dielectric constants of less than about 10 at 25° C. such as decalin, diethylether, diphenylether, dioxane, thiophene, dimethylsulfide, ethyl acetate, tetrahydroduran, chlorobenzene, bromobenzene and t-butanol, etc.

Preferably, specifically excluded from the process are substantial amounts of any highly polar solvents having high dielectric constants such as N-methylformamide, N,N-dimethylformamide, acetonitrile, nitrobenzene, γ-butyrolactone, nitromethane, dimethylsulfoxide, sulpholane and N-methylpyrrolidone, etc., and mixtures thereof.

Any mole ratio of bicyclo[2.2.1]hept-2-ene to sulfur can be employed. However, because approximately one mole of bicyclo[2.2.1]hept-2-ene react with 3 gram atoms of sulfur, a minimum mole:gram atom ratio preferably employed is one mole of 2.2.1-hept-2-ene to 3 gram atoms of sulfur.

The reaction can be carried out at any phenol:sulfur ratio, including such ratios as those within the range of from about 1:0.05 to about 1:20, however preferably ratios within the range of from about 1:1 to about 1:10, and more preferably from about 1:2 to about 1:4 are employed. Any mole ratio of phenol to base can be employed. In general, suitable ratios include the use of base in catalytic amounts, e.g. wherein the phenol:base mole ratios are as low as 1:0.001 (0.1 mole % base based on phenol), preferably at least as low as 1:0.10 (10 mole % base based on phenol) as well as noncatalytic amounts, e.g. wherein the phenol:base mole ratios are as high as 1:2 (200 mole % base based on phenol) or even higher. In general, satisfactory phenol:base proportions are within the range of from about 1:0.01 to about 1:1, more preferably from about 1:0.02 to about 1:0.20 and even more preferably from about 1:0.05 to about 1:0.10.

In general, any reaction temperature can be employed wherein the thermal reaction kinetics are not deleterious to reaction rates, reaction time, yield and/or conversion of the bicyclo[2.2.1]hept-2-ene compounds to the desired 3,4,5-trithiapolycyclo compounds. In general, the reaction temperatures can be varied widely, however, they often fall within the range of from about 0° to about 200° C., and more often fall within the temperature range of from about 80° to about 120° C.

Any reaction period can be employed, however, generally effective reaction periods fall within the range of from about ½ hour to about 5 hours. The process is preferentially carried out in the presence of an inert atmosphere of nitrogen in order to exclude from the reaction medium any oxygen or oxidizing agents which are well-known to oxidize organic sulfides to sulfoxides or sulfones among other undesirable reaction products.

The amount of solvent when employed in accordance with a preferred embodiment of this invention can be employed in any amount and can vary widely. In general, the solvent to bicyclo[2.2.1]hept-2-ene ratio which is generally suited to the process of this invention can be within the range of from about 1000:1 to about 1:1 preferably from about 100:1 to about 2:1 and even more preferably from about 10:1 to about 5:1.

Advantageously, it is desirable to preclude substantial amounts of any polar solvents having high dielectric constants such as N-methylformamide, N,N-dimethylformamide, acetonitrile, nitrobenzene, γ-butyrolactone, nitromethane, dimethylsulfoxide, sulpholane and N-methylpyrrolidone, etc. and mixtures thereof in order to avoid possible reductions in the yield of the desired 3,4,5-trithiapolycyclo compounds due to the byproduct formation of organomercaptophenols in accordance with the teachings of my copending Ser. No. 484,996, now U.S. Pat. No. 3,979,460, referred to hereinbefore. In addition, it is desirable to exclude from the reaction medium substantial quantities of activated olefins or epoxy compounds in order to avoid the preparation of undesirable byproducts thiobis-2,6-disubstituted phenols which can result in accordance with the process and teachings described in my copending Ser. No. 484,995, now U.S. Pat. No. 3,953,519, referenced hereinbefore.

By the practice of this invention, as described hereinbefore, 3,4,5-trithiapolycyclo compounds can be prepared having the following structural formula:

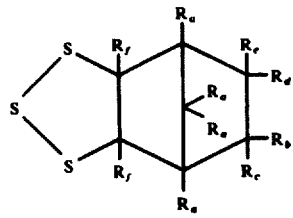

It was found that the exo-form of these compounds is produced by this invention. Illustrative of compounds falling within the immediately preceding formula one can mention:

exo-3,4,5-trithiatricyclo[5.2.1.0$^{2,6}$]decane,
exo-3,4,5-trithiatetracyclo[5.5.1.0$^{2,6}$.0$^{8,12}$]-tridec-9ene,
8-vinyl-exo-3,4,5-trithiatricyclo[5.2.1.0$^{2,6}$]-decane,
8-ethylidene-exo-3,4,5-trithiatricyclo[5.2.1.0$^{2,6}$]-decane,
8-methyl-exo-3,4,5-trithiatricyclo[5.2.1.0$^{2,6}$]-decane,
8,9-dimethyl-exo-3,4,5-trithiatricylo[5.2.1.0$^{2,6}$]-decane,
8-hydroxy-exo-3,4,5-trithiatricyclo[5.2.1.0$^{2,6}$]-decane,
8,9-dihydroxy-exo-3,4,5-trithiatricyclo[5.2.1.0$^{2,6}$]-decane,
exo-3,4,5-trithiatricyclo[5.2.1.0$^{2,6}$]decan-exo-8-methanol,
exo-3,4,5-trithiatricyclo[5.2.1.0$^{2,6}$]decan-endo-8-methanol,
8,9-dihydroxymethyl-exo-3,4,5-trithiatricyclo-[5.2.1.0$^{2,6}$]decane,
8-decyl-exo-3,4,5-trithiatricyclo[5.2.1.0$^{2,6}$]decane,
8,9-di-(aminomethyl)-exo-3,4,5-trithiatricyclo-[5.2.1.0$^{2,6}$]decane,
1-nonyl-exo-3,4,5-trithiatricyclo[5.2.1.0$^{2,6}$]decane,
8-methyl-8-ethyl-exo-3,4,5-trithiatricyclo-[5.2.1.0$^{2,6}$]decane,
8,8,9,9-tetramethyl-exo-3,4,5-trithiatricyclo-[5.2.1.0$^{2,6}$]decane,
8-phenyl-exo-3,4,5-trithiatricyclo[5.2.1.0$^{2,6}$]-decane,
8-cyclopentyl-exo-3,4,5-trithiatricyclo[5.2.1.0$^{2,6}$]-decane,
8-(3-butenyl)-exo-3,4,5-trithiatricyclo[5.2.1.0$^{2,6}$]-decane,
8-methyl-9-ethylidene-exo-3,4,5-trithiatricyclo-[5.2.1.0$^{2,6}$]decane,
8-methyl-9-methylene-exo-3,4,5-trithiatricyclo-[5.2.1.0$^{2,6}$]decane,
8-(5-hexenyl)-9-methyl-exo-3,4,5-trithiatricyclo-[5.2.1.0$^{2,6}$]decane,
and the like.

The 3,4,5-trithiapolycyclic compounds produced can be used to produce sulfur-containing polymers containing the repeating unit of the average formula:

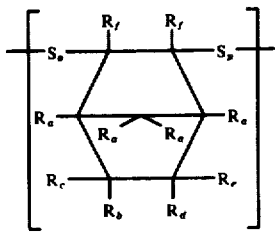

in the polymer chain, wherein $$(o + p)/2$$

has a value of 3. The polymers are generally solids with average molecular weights ranging up to about 1,000 or more. The polymers can be used as additives for lubricants and can also be used to produce protective coatings on solid substrates or to produce fibers and films. The polymers can be produced by methods well-known to those skilled in the art such as those set out in the before referenced Kurtz et al. patent U.S. Pat. No. 3,586,700.

In order that those skilled in the art may better understand my invention, the following examples are given which are illustrative of the best mode of practicing this invention, however, these examples are not intended to limit the invention in any manner whatsoever. In all of the examples -- all parts are by weight unless otherwise stated -- the following general procedure was employed. For purposes of brevity, only deviations from this procedure will be set out in the examples.

GENERAL PROCEDURE

A metal phenolate, e.g. sodium 2,6-dimethylphenolate, is prepared by adding sodium to a phenol, e.g. 2,6-dimethylphenol. The mixture is heated to elevated temperatures, e.g. about 100° C. until the sodium is dissolved. The mixture is cooled, e.g. to a temperature of about 100° C. and sulfur, e.g. elemental sulfur (flowers of sulfur), a bicyclo[2.2.1]hept-2-ene compound, e.g. bicyclo[2.2.1hept-2-ene is added to the sodium phenolate solution. The resulting mixture is heated to elevated temperatures, e.g. temperatures of about 100° C. and maintained there over an extended period of time, e.g. from 1 to 7 hours. The reaction mixture, generally, is not homogeneous and vigorous stirring is required. After heating, the resulting reaction mixture is cooled and diluted, if necessary, with a suitable diluent, e.g. ether, and is washed with base, e.g. a 10% sodium hydroxide solution, to remove the phenol. The resulting product after removal of the solvent is purified by vacuum distillation. The 3,4,5-trithiapolycyclo compounds, e.g. exo-3,4,5-trithiatricyclo[5.2.1.0$^{2,6}$]-decane, is recovered and characterized by melting point in both crude and purified form, mass spectroscopy, and nuclear magnetic resonance.

The results of a series of runs are set out in Table I, Run Nos. 1-3, which follows:

TABLE I

Summary of Experimental Data - Run Nos. 1-3

| Run No. | Reaction Products Composition | Yield | Reactants(R), Metal(M), Phenol(P), Solvent(S) | | Conv. | Temp. | Time | Mole Ratios Bicyclo 2.2.1 hept-2-ene:Sulfur:Metal: Phenol |
|---|---|---|---|---|---|---|---|---|
| 1. | (A) exo-3,4,5-trithiatricyclo-[5.2.1.0$^{2,6}$]decane<br>(I) Analysis<br>  (a) NMR<br>  (b) Mass.Spec. MW 190<br>  (c) VPC: ~3% of 3<br>Other unidentified compounds | 73.6% | (R) bicyclo[2.2.1]-hept-2-ene,<br>sulfur<br>(M) metallic sodium<br>(P) 2,6-xylenol | 95.11g(1.0 m)<br><br>48.0 g(1.5 m)<br>1.2 g(0.05m)<br>122.16g(1.0 m) | 100% | 100° C | 6 hrs | 1:1.5:0.05:1.0 |
| 2. | (A) exo-3,4,5-trithiatricyclo-[5.2.0$^{2,6}$]decane<br>(I) Analysis<br>  (a) NMR<br>  (b) Mass.Spec. MW 190<br>  (c) VPC | 38.6% | (R) bicyclo 2.2.1-hept-2-ene,<br>sulfur<br>(M) metallic sodium<br>(P) phenol | 94.16g(1.0 m)<br><br>96.0 g(3.0 m)<br>1.2 g(0.05m)<br>94.1 g(1.0 m) | 100% | 100° C | 7 hrs | 1.0:3.0:0.05:1.0 |
|  | (B) 3-thiatricyclo[3.2.1.0$^{2,4}$]-octane<br>(I) Analysis<br>  (a) NMR: C$^{13}$<br>  (b) Mass.Spec. MW 126<br>  (c) VPC | 9.4% | | | | | | |
|  | (C) bis(bicyclo[2.2.1]heptan-2-yl)sulfide<br>(I) Analysis<br>  (a) NMR<br>  (b) Mass.Spec. MW 222<br>  (c) VPC | trace | | | | | | |
| 3. | (A) exo-3,4,5-trithiatetra-cyclo[5.5.1.0$^{2,6}$.08,12]-tridec-9-ene<br>(I) Analysis<br>  (a) NMR<br>  (b) Mass.Spec.<br>  (c) VPC | 48.3% | (R) tricyclo [5.2.0$^{3,9}$]deca-2,6-diene,<br>sulfur<br>(M) metallic sodium<br>(P) 2,6-xylenol | 132.3g(1.0 m)<br><br><br>96.0g(3.0 m)<br>1.2g(0.05m)<br>122.1g(1.0 m) | 100% | 140° C | 1 hr | 1:3:0.05:1.0 |

Other modifications and variations of the present invention are possible inlight of the above teachings. It is, therefore, to be understood that changes may be made in the particular embodiments of the invention described which are within the full intended scope of the invention as defined by the appended claims.

I claim:

1. A process for the preparation of a 3,4,5-trithiapolycyclo compound which comprises the reaction of sulfur with a bicyclo[2.2.1]hept-2-ene compound of the formula:

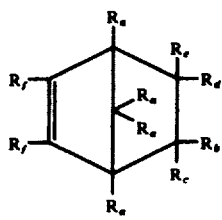

wherein each $R_a$, $R_b$, $R_c$, $R_d$ and $R_e$ when taken singly can be hydrogen, halogen, alkyl of from 1 to about 15 carbon atoms, aryl of from 6 to about 15 carbon atoms, and cycloalkyl of from 4 to about 10 carbon atoms; $R_b$ and $R_d$ when taken singly can be alkenyl of from 2 to about 10 carbon atoms, hydroxyl, hydroxyalkyl of from 1 to about 10 carbon atoms, dialkylamino of from 1 to about 10 carbon atoms, dialkylaminoalkyl of from 1 to about 4 carbon atoms per alkyl group, and alkoxy of from 1 to about 10 carbon atoms; $R_f$ can be hydrogen or alkyl of from 1 to about 15 carbon atoms; $R_b$ and $R_c$ taken together and $R_d$ and $R_e$ taken together can be alkylidene of from 1 to about 6 carbon atoms; $R_b$ and $R_d$ taken together are the divalent —CHYCH=CY— group in which Y is hydrogen or methyl, said reaction being carried out at a temperature within the range of from about 0° to about 200° C. in the presence of a phenol of the formula:

wherein Ar is an arene radical having a valence of at least one and having at least one —OH radical attached directly to an arene carbon atom, R is an alkyl, cycloalkyl, aryl, halide, hydroxy, alkoxy, alkanoate radical or a combination thereof, m is a positive integer at least equal to 0, and n is a positive integer at least equal to 1, and a base selected from the group consisting of elemental alkali and alkaline earth metals, alkali or alkaline earth metal hydroxides, and salts of strong bases and weak organic acids.

2. The process of claim 1, wherein the process is carried out in the presence of an inert organic solvent.

3. The process of claim 2, wherein the amount of base used is less than 10 mole percent based on phenol.

4. The process of claim 1, wherein the sulfur is sublimed sulfur.

5. The process of claim 1, wherein the phenol is 2,6-dimethylphenol.

6. The process of claim 1, wherein the 3,4,5-trithiapolycyclo compound is exo-3,4,5-trithiatricyclo-[5.2.1.0$^{2,6}$]decane.

7. The process of claim 1, wherein the 3,4,5-trithiapolycyclo alkane compound is 3-thiatricyclo[3,2,1.0$^{2,4}$]-octane.

* * * * *